US009839562B2

(12) United States Patent
Brown et al.

(10) Patent No.: US 9,839,562 B2
(45) Date of Patent: Dec. 12, 2017

(54) DIAPER WITH SEPARATOR SHEET

(71) Applicant: The Procter & Gamble Company, Cincinnati, OH (US)

(72) Inventors: Darrell Ian Brown, Mason, OH (US); Sandra Freiboth, Leiderbach (DE); Rolf Hecker, Kriftel (DE); Cornelia Beate Martynus, Nidderau-Osteim (DE); Janet Neton, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 747 days.

(21) Appl. No.: 14/171,037

(22) Filed: Feb. 3, 2014

(65) Prior Publication Data

US 2014/0221955 A1 Aug. 7, 2014

Related U.S. Application Data

(63) Continuation of application No. 61/759,478, filed on Feb. 1, 2013.

(51) Int. Cl.
| | |
|---|---|
| *A61F 13/15* | (2006.01) |
| *A61F 13/20* | (2006.01) |
| *A61F 13/49* | (2006.01) |
| *A61F 13/494* | (2006.01) |
| *A61F 13/495* | (2006.01) |

(52) U.S. Cl.
CPC .. *A61F 13/49019* (2013.01); *A61F 13/15593* (2013.01); *A61F 13/15756* (2013.01); *A61F 13/495* (2013.01); *A61F 13/49017* (2013.01); *A61F 13/49413* (2013.01); *A61F 13/49446* (2013.01); *A61F 2013/49022* (2013.01); *A61F 2013/4948* (2013.01); *A61F 2013/4951* (2013.01); *A61F 2013/4956* (2013.01)

(58) Field of Classification Search
CPC .......... A61F 13/49017; A61F 13/49019; A61F 13/49413; A61F 2013/4951; A61F 2013/4956

See application file for complete search history.

(56) References Cited

U.S. PATENT DOCUMENTS

| | | | |
|---|---|---|---|
| 6,010,490 A | 1/2000 | Freeland et al. | |
| 6,843,134 B2 | 1/2005 | Anderson et al. | |
| 7,062,983 B2 | 6/2006 | Anderson et al. | |
| 7,722,587 B2 | 5/2010 | Suzuki et al. | |
| 7,918,838 B2 | 4/2011 | Minato et al. | |
| 8,168,853 B2 | 5/2012 | Autran et al. | |
| 8,197,457 B2 * | 6/2012 | Suzuki | A61F 13/495 604/385.24 |
| 9,050,218 B2 * | 6/2015 | Martynus | A61F 13/49406 |
| 9,050,219 B2 * | 6/2015 | Martynus | A61F 13/4902 |
| 2007/0156110 A1 | 7/2007 | Thyfault | |
| 2012/0035576 A1 | 2/2012 | Ichikawa et al. | |

OTHER PUBLICATIONS

"Abut." Dictionary.com. 2017. https://www.dictionary.com (Apr. 16, 2017).*
PCT International Search Report, dated Apr. 28, 2014 (10 pages).

* cited by examiner

*Primary Examiner* — Michele M Kidwell
(74) *Attorney, Agent, or Firm* — William E. Gallagher

(57) ABSTRACT

Diapers, including infant diapers, training pants, and adult incontinence articles, and the like having a specific elastically stretchable transverse separator sheet for excrement separation and/or isolation away from the skin, and process for making the same.

8 Claims, 6 Drawing Sheets

DIAPER WITH SEPARATOR SHEET

FIELD OF THE INVENTION

This invention is directed to diapers, including infant diapers, training pants, and adult incontinence articles, and the like having a specific elastically stretchable transverse separator sheet for excrement separation and/or isolation away from the skin.

BACKGROUND OF THE INVENTION

Several diaper types have been proposed with components to reduce leakage of feces and urine from the diaper, to reduce soiling of the genitals or other skin by the feces, or to reduce mixing of urine and feces, to further reduce the risk of irritation of the skin. For example, diapers with a topsheet with an opening, providing a passageway to a void space for collected feces and urine have been proposed; also proposed are diapers with two openings to receive the urine and feces in separate areas; also proposed are diapers with a transversely positioned three-dimensional resilient barrier wall or partition placed in the centre of the diaper, to receive feces and urine respectively on either side of said wall or partition, and to avoid migration of the feces to the front of the article, beyond the separator, or combinations of the above solutions. An example of such a topsheet structure with longitudinal elasticated portions and a transverse portion with a partition is described in for example U.S. Pat. No. 7,918,838; however, such large structures may add significant cost to the product. Furthermore, if the central partition portion is too large, there is a risk that, upon misplacement of the diaper, feces or urine is received on this portion. Simpler transversely positioned partitions are for example described in EP 674499, which describes transverse sheet material attached to the longitudinal cuffs of the article.

The inventors found however that, whilst such transversely positioned separators attached to cuffs may be beneficial from a cost point of view, its success in use (e.g. correct application; performance when the wearer moves) is dependent on its design; and furthermore, such separators are not easily processable into a diaper. In fact, certain features that may be desirable from a performance and product point of view may be very difficult or expensive from a process point of view. The inventors found that such transversely positioned separators are preferably elastic or elasticated. However, applying an elastic or elasticated piece of material, with elasticity in cross-machine direction may create difficulties and adds process complexity.

The inventors have now found improved diapers with an improved and optimized transversely positioned elastically extensible separator that has specific elastic behavior to deliver optimized in-use performance, (both when the wearer moves or is at rest, and both when the wearer's legs are close together or far apart) and that importantly, allows application into the diaper by means of process steps that add little extra complexity or cost, and the invention accordingly also provides processes for making such diapers.

SUMMARY OF THE INVENTION

The invention relates to an infant or adult diaper having a longitudinal centerline and a lateral centerline perpendicular to the longitudinal centerline. The diaper comprises a topsheet and a backsheet and positioned therein between an absorbent core, and a first and second longitudinally extending opposing elastic cuffs, positioned on either longitudinal side of the topsheet. Each of the diaper, topsheet, backsheet, absorbent core and elastic cuffs have a crotch region, positioned in between a front region and a back region. The diaper comprises a transverse separator sheet made of a separator sheet material. The transverse separator sheet has a transversely extending top edge and top edge portion and an opposing transversely extending bottom edge and bottom edge portion. Parts of the top edge portion are attached to the cuffs in the crotch regions or front regions of the cuffs thereof by means of attaching a first attachment area of the top edge portion to the crotch region or front region of the first cuff and a second opposing attachment area of the top edge portion to the crotch region or front region of the second cuff, to form a first cuff attachment area and a second cuff attachment area. Each cuff attachment area has an inner edge towards the longitudinal centerline of the diaper. Part(s) or all of the bottom edge portion are attached to the topsheet with at least one topsheet attachment area. The separator sheet's minimum transverse dimension in relaxed state of the separator sheet between the opposing inner edges of the first and second cuff attachment areas is at least 20 mm. The separator sheet's minimum longitudinal dimension in relaxed state of the separator sheet between the top edge and the bottom edge of the separator sheet is at least 30 ram. The transverse separator sheet has a transverse strain of 0.8 at a first cycle extension force of 1.0N or less, as measured according to the in-use two-cycle hysteresis test. The transverse separator sheet has also 30% set or less after having been extended to a transverse strain of 0.8, as measured according to the in-use two-cycle hysteresis test. Furthermore, the transverse separator sheet is elastically extensible in the transverse direction to a strain of at least 0.8, as measured according to the in-process two-cycle hysteresis test.

The invention also relates to a process for making such an infant or adult diaper or a diaper portion comprising the steps of:

a) obtaining a pair of longitudinally extending opposing elastic cuffs, travelling in machine direction (MD), that are preferably in stretched state, whereby there is a first average transverse spacing distance $D_1$ between the opposing cuffs in the crotch region thereof;

b) obtaining an elastically extensible separator sheet material in relaxed state having a top edge portion and an opposing bottom edge portion, substantially perpendicular to the longitudinal dimension of the cuffs;

c) partially attaching the top edge portion of the separator sheet material in relaxed state to respectively the cuffs' crotch regions or front regions, by means of attaching a first attachment area of the top edge portion to the crotch region or front region of a first cuff of a pair, and a second opposing attachment area of the top edge portion to the crotch region or front region of the second cuff of a pair, to form a first cuff attachment area and a second cuff attachment area;

d) obtaining a topsheet;

e) attaching the separator sheet material's bottom edge portion or part thereof to the topsheet;

f) spreading apart the cuffs in the transverse direction perpendicular to the longitudinal dimension of the cuffs to obtain cuffs with an average second transverse spacing distance $D_2$ between them in at least the crotch region, the average second distance $D_2$ being preferably at least 1.8 times the average first distance $D_1$;

g) attaching, prior to step c), or subsequently to any of steps c), e) or f), or simultaneously with step c) or e), the opposing cuffs to the topsheet, or backsheet, or absorbent core, by attaching a first cuff along a first longitudinal side thereof and a second cuff or cuff web along a second longitudinal side thereof;

h) optionally further attaching the bottom edge portion that is partially attached to the topsheet in step e) to the topsheet.

The invention also relates to a diaper or diaper portion made by said process.

LED DESCRIPTION OF THE INVENTION

Figure 1:
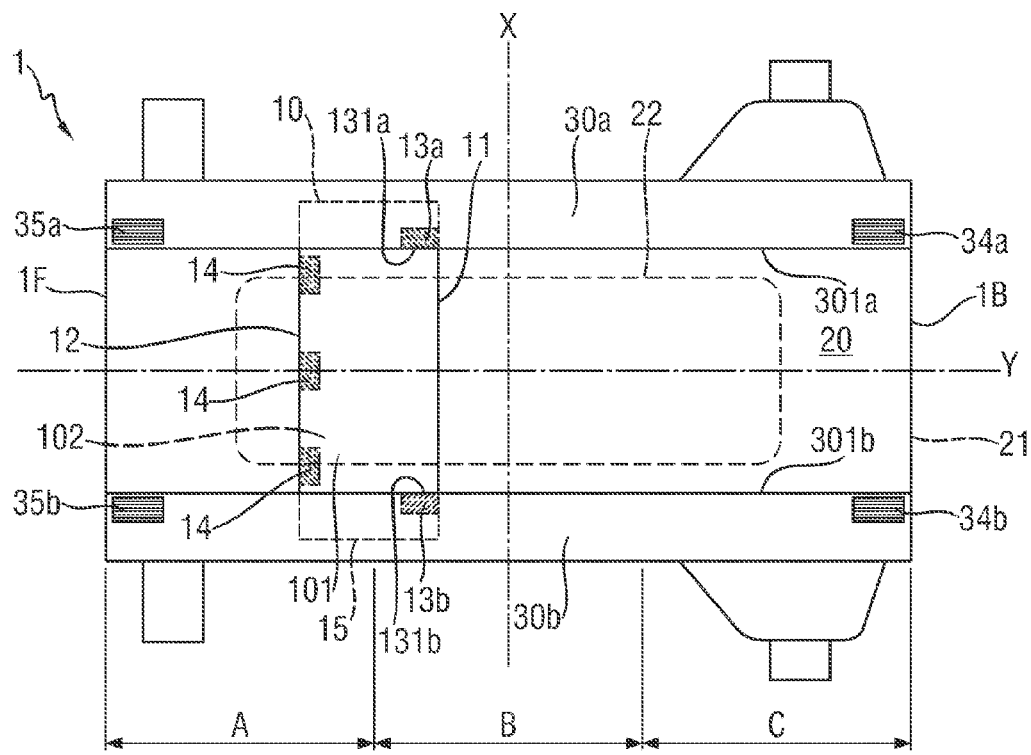
FIG. 1 shows a top view of a diaper according to an embodiment of the present invention in flat state.
Figure 2:
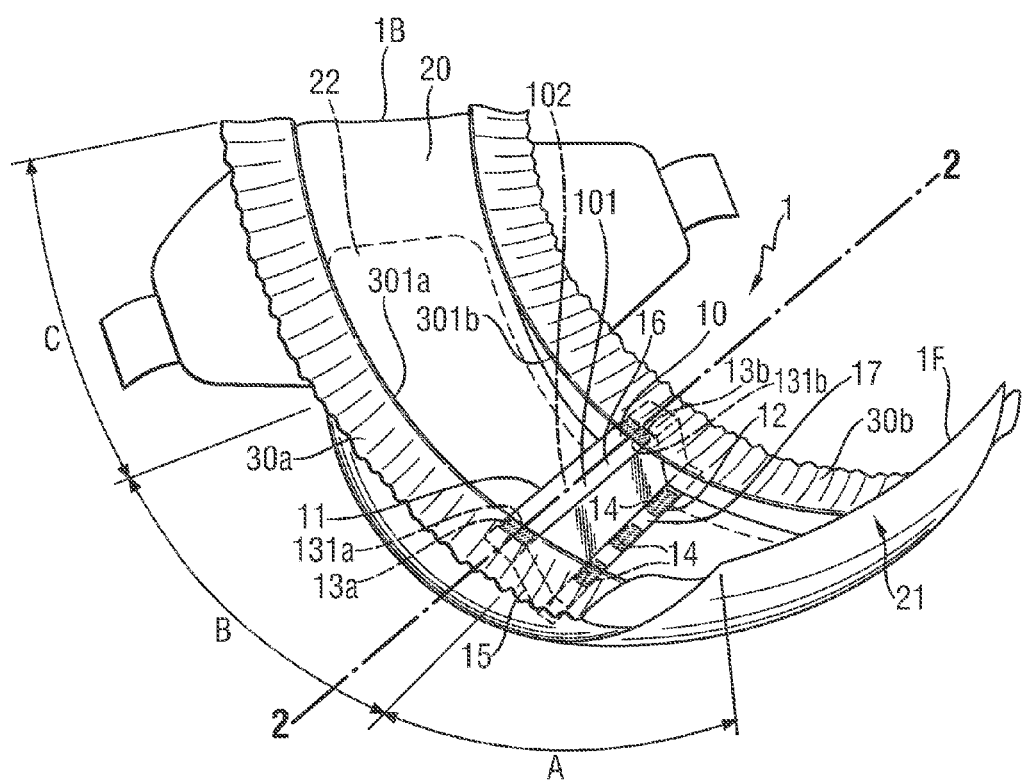
FIG. 2 shows a perspective view of the diaper of FIG. 1.

"Diaper" is used herein, to refer to absorbent articles to be placed about the wearer's tower torso, and include infant (baby and toddler) diapers and adult diapers, and it includes so-called diapers with fasteners, to be fastened around the lower torso, and pant-type diapers.

"Diaper portion" is used herein to refer to a portion of the diaper comprising at least the topsheet, the transverse separator sheet and the two elastic cuffs.

"Front region" (A) and 'back region' (C) are used herein to refer to the two regions, which are in use, respectively, the closest to the front of the wearer and the back of the wearer, each spanning the transverse dimension of the diaper or diaper portion or element thereof, e.g. elastic cuff or topsheet, and each region having a longitudinal dimension that is one third of the longitudinal dimension of the diaper or diaper portion or element thereof, e.g. elastic cuff or topsheet.

"Crotch region" is used herein to rk.*r to the region positioned between the front region and the back region, having also a longitudinal dimension that is one third of the longitudinal dimension of the diaper, diaper portion or element thereof, e.g. elastic cuff or topsheet.

"Longitudinal" is used herein to refer to the direction which is running substantially parallel or exactly parallel to the longitudinal centerline (Y) of the diaper or diaper portion or topsheet, which may be the machine direction (MD) of the process.

"Lateral" or "transverse" is used herein to refer to the direction which is substantially perpendicular or exactly perpendicular to the longitudinal centerline (Y) of the diaper or diaper portion or topsheet, which may be the cross-machine direction of the process (CD).

"Z-direction" is used herein to refer to the direction perpendicular to the longitudinal direction and perpendicular to the transverse or lateral direction.

"Longitudinal dimension", "transverse dimension" or "Z-dimension" is used herein to refer to the dimension of the diaper, diaper portion or element thereof, e.g. elastic cuff or topsheet or transverse separator sheet or transverse separator sheet material, which is measured respectively in the longitudinal direction, transverse direction or Z-direction of the diaper or diaper portion or element thereof, e.g. elastic cuff or topsheet or transverse separator sheet or transverse separator sheet material.

"Substantially perpendicular" or "substantially parallel" is used herein to refer to directions within 30° or 20° or 10° or 5° from the exact perpendicular or parallel direction, unless stated or specified otherwise.

As used herein, "along" means at least partially substantially parallel to and adjacent to.

"Top edge" or "top edge portion" is used herein to refer to respectively the transversely extending edge or transversely extending edge portion of the separator sheet or separator sheet material which is in contact with the wearer's body when the diaper 1 is applied to a wearer.

"Bottom edge" or "bottom edge portion" is used herein to refer to respectively the transversely extending edge or transversely extending edge portion of the separator sheet or separator sheet material which is more remote from the wearer's body (compared to the top edge or top edge portion) when the diaper is applied to a wearer.

"Relaxed" or "relaxed state" or "contracted" or "contracted state" is used herein to refer to the state of the diaper or diaper portion or separator sheet or separator sheet material wherein no forces are applied to respectively the diaper or diaper portion or separator sheet or separator sheet material.

"Flat state" is used herein to refer to the state of the diaper when the diaper is laid out flat onto an even horizontal surface.

"Distal edge" is used herein to refer to the longitudinally extending edge of an elastic cuff which in use is closer to the wearer's body than the other longitudinally extending edge of the same elastic cuff.

"Strain" is used herein to refer to the engineering strain which is defined hereinafter in the test methods section of this application.

"Bonding pattern density" is used herein to refer to the percentage of the surface area of a cuff attachment area or a topsheet attachment area which is covered with the one or more individual bond(s) which are comprised by the cuff attachment area or the topsheet attachment area.

The diaper 1 according to the present invention has a longitudinal centerline Y and a lateral centerline X perpendicular to the longitudinal centerline Y. The diaper 1 comprises a topsheet 20, a backsheet 21 and positioned therein between an absorbent core 22. The diaper 1 further comprises a pair of longitudinally extending opposing elastic cuffs 30a, 30b positioned on either longitudinal side of the topsheet 20. Each of the diaper 1, topsheet 20, backsheet 21, absorbent core 22 and elastic cuffs 30a, 30b have a crotch region B positioned in between a front region A and a back region C.

The diaper 1 comprises a transverse separator sheet 10 made of a separator sheet material 15 as for example shown in FIGS. 1 to 7.

Transverse Separator Sheet and Material

The transverse separator sheet 10 herein is an individual sheet that is attached (e.g. in attachment steps, e.g. as part of the process of the invention as described herein) to a pair of opposing elastic cuff 30a, 30b and to a topsheet 20. The separator sheet 10 (prior to attachment to the cuffs 30a, 30b or topsheet 20 is herein referred to as separator sheet material 15. The separator sheet material 15 may be cut from a separator sheet material web.

The separator sheet 10 may be present in the front region A and/or crotch region B of the diaper 1 or diaper portion; if present in the front region A of the diaper 1 or diaper portion, it is in close proximity to the crotch region B, in the back half of the front region A of the diaper 1 or diaper portion. For example, the minimum distance between the topsheet attachment area(s) 14 and the front edge 1F of the topsheet 20 or diaper 1 or diaper portion may be from 20%, or 25%, or 30% to 60%, or to 50% or to 40% of the average longitudinal dimension (average length) of the topsheet 20, diaper 1 or diaper portion, respectively.

The separator sheet 10 and separator sheet material 15 have first and second transversely extending, opposing, edges and edge portions, herein referred to as a top edge 11 and top edge portion 16, and as a bottom edge 12 and bottom edge portion 17. The top edge 11 and bottom edge 12 are connected to one another by two opposing side edges of the separator sheet 10 or separator sheet material 15. It should be understood that the two opposing side edges of the separator sheet material 15 which connect the top edge 11 to the bottom edge 12 of the separator sheet material 15 may be substantially perpendicular to the top edge 11 of the separator sheet material 15, when the separator sheet material 15 is laid out flat in relaxed, contracted state onto an even horizontal surface. It should also be understood that some portions of the two opposing side edges of the separator sheet 10 which connect the top edge 11 to the bottom edge 12 of the separator sheet 10 may have in use a. Z-direction orientation.

The separator sheet material 15 has when laid out flat onto an even horizontal surface in relaxed, contracted state, a longitudinal dimension (length), also referred to as the separator sheet's longitudinal dimension (length) in relaxed state of the separator sheet 10 and the separator sheet material 15 has when laid out flat onto an even horizontal surface in relaxed, contracted state, a transverse dimension (width), also referred to as the separator sheet's transverse dimension (width) in relaxed state of the separator sheet 10. It should be understood that the width of the separator sheet 10 or separator sheet material 15 may be longer than the length of respectively the separator sheet 10 or separator sheet material 15.

The separator sheet 10 may have a minimum longitudinal dimension in relaxed state of the separator sheet 10 between the top edge 11 and the bottom edge 12 of the separator sheet 10 of from 3.0 cm, or from 4.0 cm, or from 5.0 cm, to for example 15.0 cm, or to 10.0 cm, or to 8.0 cm or to 7.0 cm, or to 6.0 cm or to 5.1 cm.

The separator sheet 10 may have an average transverse dimension in relaxed state of the separator sheet 10 of at least 2.5 cm, or at least 4.0 cm, or at least 5.0 cm to less than 12.0 cm or less than 10.0 cm.

The top and bottom edge portions 16, 17, as referred herein, extend over the whole transverse dimension of the separator sheet 10 or separator sheet material 15 and may have each an average longitudinal dimension of 3% to 50% or 10% to 40% or 10% to 25% of the minimum longitudinal dimension of the separator sheet 10.

The separator sheet 10 is elastically extensible in at least the transverse direction, i.e. is able to extend upon application of a force, and to contract to about its original width upon release of said force, as described hereinafter. Only the top edge portion 16 of the separator sheet 10 may be elastically extensible in at least the transverse direction.

The separator sheet 10 may also be elastically extensible in the longitudinal direction.

The separator sheet 10 may be made of an elasticated sheet material 15, rendering the separator sheet 10 elastically extensible in the transverse direction at least.

"Elasticated" when used herein for the separator sheet 10 or separator sheet material 15 (and also for the cuff or cuff web material) means that it is made of an inelastic sheet material that has been provided only in a specific area or in specific areas, i.e. the elasticated area(s), with an elastic material, e.g. one or more elastic bands or strands. The total surface area of the elasticated areas may for example be less than 50% of the total surface area of the separator sheet 10 or separator sheet material 15.

One or both of the top and bottom edge portions 16, 17 of the separator sheet 10 or separator sheet material 15 may be elasticated by application of one or more elastic band(s) or strand(s) extending substantially in transverse direction to a sheet material that may be inelastic e.g. an inelastic nonwoven sheet.

The separator sheet 10 may be elastically extensible in transverse direction at least. It may be elastically extensible in transverse direction at least over its surface area excluding the surface areas that are attached to the cuffs 30a, 30b and topsheet 20.

The separator sheet material 15 may be or may comprise an elastic film or a nonwoven sheet material or a laminate of an elastic film and a nonwoven sheet material. The nonwoven sheet material of the laminate can be positioned such that it is in contact with the skin of the wearer. Such a configuration of the laminate may provide more comfort to the wearer than when the elastic film is directly in contact with the skin of the wearer.

The nonwoven sheet material may be made of polyolefins known in the art, such as polyethylene and/or polypropylene, made into fibers, including bicomponent fibers that are then made into a nonwoven sheet. The nonwoven sheet material may be a necked nonwoven. The nonwoven sheet material may be a meltblown nonwoven or spunbond nonwoven or carded nonwoven; it may be a laminate thereof; for example it may be a laminate of spunbond or carded layer or layers and meltdown nonwoven layer(s).

The separator sheet material 15 may be or comprise a nonwoven sheet material that has a substantially uniform elastic behavior due to the application (e.g. substantially uniformly) of an elastic material to the nonwoven sheet material, in a way that it provides elasticity at least in transverse direction to the nonwoven sheet material; for example, elastic material may be sprayed or extruded onto a nonwoven sheet material, e.g. homogeneously or in a pattern such as stripes in transverse direction.

The separator sheet material 15 may be rectangular or square when laid out flat in relaxed, contracted state onto an even horizontal surface in relaxed, contracted state. The separator sheet material 15 may also be trapezoid when laid out flat in relaxed, contracted state onto an even horizontal surface in relaxed, contracted state, the top edge 11 and the bottom edge 12 of the separator sheet material 15 forming the two parallel sides of the trapezoid.

The separator sheet material 15 may be a barrier material; it may be hydrophobic; e.g. it may be hydrophilic and made hydrophobic with a hydrophobic surface coating, such as known in the art, for example a wax or a hydrophobic surface coating comprising one or more silicone polymers or fluorinated polymers.

The separator sheet 10 has an elastic behavior such that it can be elastically extensible in transverse direction at least, during the process of making the diaper 1 or diaper portion herein, and during application of the diaper 1 on the wearer, whilst providing in in-use conditions (during wear) correct alignment with the skin of the wearer, both when the wearer moves the legs apart and when the wearer moves the legs together. The separator sheet 10 should furthermore preferably have a certain tension in use to ensure it forms an effective separator (barrier) with a Z-direction dimension, to avoid migration of feces from the back to the front of the diaper 1. Furthermore, this tension should not be too high, otherwise the cuffs 30a, 30b, to which the separator sheet 10 is attached, are in use pulled too close together, leading to potential leakage issues of urine or feces outside or onto the cuffs 30a, 30b.

The separator sheet 10 has a transverse strain of 0.8 (extension to at least 1.8 times its width) at a first cycle extension force of 1.0 N or less, as measured according to the in-use two-cycle hysteresis test as described herein below. The separator sheet 10 may have a transverse strain of 1.2 (extension to at least 2.2 times its width) at a first cycle extension force of 1.5 N or less, or at a first cycle extension force of 1.0N or less, as measured according to the in-use two-cycle hysteresis test. The separator sheet 10 may have a transverse strain of 0.8 or 1.2 at a first cycle extension force of 0.8 N or less, or at a first cycle extension force of 0.6 N or less, but typically at a first cycle extension force of at least 0.2 N, or at least 0.3 N, as measured according to the in-use two-cycle hysteresis test. Hence, the separator sheet 10 is such that when the wearer spreads the legs, the elastic cuffs 30a, 30b can expand and move outwards without being too restricted by the separator sheet's elastic forces. This ensures the elastic cuffs 30a, 30b can stay in place and reduces the risk of feces leakage over the elastic cuffs 30a, 30b.

The separator sheet 10 has 30% set or less after having been extended to a transverse strain of 0.8, as measured according to the in-use two-cycle hysteresis test. The separator sheet 10 may have 30% set or less after having been extended to a transverse strain of 1.2, as measured according to the in-use two-cycle hysteresis test. The separator sheet 10 may have 20% set or less after having been extended to a transverse strain of 0.8 or 1.2, as measured according to the in-use two-cycle hysteresis test. It may have 10% set or less after having been extended to a transverse strain of 0.8 or 1.2, as measured according to the in-use two-cycle hysteresis test. Hence, the transverse separator sheet 10 is such that in use, when the wearer moves the legs together, the transverse separator sheet 10 can contract to a very small dimension very quickly, thus avoiding slack in the separator sheet 10, and hence reducing the risk of feces leakage over the separator sheet 10. Therefore, the separator sheet 10 remains in contact with the skin of the wearer during use, so both when the wearer moves and spreads the legs and when the wearer rests and closes the legs.

The separator sheet 10 is elastically extensible in the transverse direction to a strain of at least 0.8, as measured according to the in-process two-cycle hysteresis test. The separator sheet 10 or separator sheet material 15 may be elastically extensible in the transverse direction to a strain of at least 1.2 or at least 1.5 or at least 2.0 or at least 2.5 or at least 3.0 or at least 3.5, as measured according to the in-process two-cycle hysteresis test. This can be done with any force suitable for processing elastic materials, typically a force of 20 N or less, or typically a force of 10N or less. Therefore, the separator sheet 10 is such that it can be processed in a process that requires high extension, and that it contracts about immediately to about its original width, to allow high speed of processing.

It should be understood that the separator sheet 10 is considered as being elastically extensible in the transverse direction to a certain strain value if after having been extended to said strain value according to the in-process two-cycle hysteresis test, the percent set measured according to the in-process two-cycle hysteresis test is of 30% set or less or 20% or less or 10% or less. Having such a low set value ensures that the separator sheet material 15 is not damaged during processing of the diaper 1.

Attachment of the Separator Sheet to the Elastic Cuffs

Parts of the top edge portion 16 of the separator sheet 10 are attached to the elastic cuffs 30a, 30b in the crotch region B or front region A of the elastic cuffs 30a, 30b thereof. A first cuff attachment area 13a and a second cuff attachment area 13b are formed by attaching respectively a first attachment area of the top edge portion 16 to the crotch region or front region of the first cuff 30a and a second opposing attachment area of the top edge portion 16 to the crotch region or front region of the second cuff 30b. Each of the first and second cuff attachment areas 13a, 13b has an inner edge 131a, 131b which is the edge of attachment area 13a, 13b which is the closest to the longitudinal centerline Y of the topsheet 20 or diaper 1. Thus, there is a (central) part of the top edge portion 16 which is not attached to either of the cuffs 30a, 30b. The minimum transverse dimension of this (central) part of the separator sheet 10 in relaxed, contracted state of the separator sheet 10, i.e. the separator sheet's minimum transverse dimension in relaxed state of the separator sheet 10 measured between the opposing inner edges 131a, 131b of the first and the second cuff attachment areas 13a, 13b is at least 20 mm, or at least 30 mm. It may be up to 60 mm, or up to 55 mm or up to 50 mm or up to 45 mm.

As mentioned hereinbefore, the top edge 11 and bottom edge 12 of the separator sheet 10 or separator sheet material 15 are connected to one another by two opposing side edges of the separator sheet 10 or separator sheet material 15. The two opposing side edges of the separator sheet 10 or separator sheet material 15 may be completely attached to each of the first and second cuffs 30a, 30b. Alternatively, only a distal end part of each of the opposing side edges may be attached to the longitudinally extending distal edge of each of the first and second cuffs 30a, 30b.

The attachment of the separator sheet 10 to the elastic cuffs 30a, 30b can be done by adhesive bonding, pressure bonding, ultrasonic bonding or any other attachment mean known in the art. A cuff attachment area 13 may comprise one or more individual bond(s). Such individual bond(s) may be arranged according to a certain bonding pattern.

It should be understood that if a cuff attachment area 13 comprises more than one individual bond, these are herein considered as a single unitary cuff attachment area.

The bonding pattern density of the first and/or second cuff attachment area(s) 13a, 13b may be more than 20%, or more than 30%, or more than 40%, or more than 60%, up to 100%.

The cuff attachment areas 13 may have any shape. They may have a rectangular shape as shown for example in FIGS. 1 to 7. The inner edge 131 of such rectangular shaped cuff attachment areas 13 may be oriented parallel to the longitudinal centerline Y of the diaper 1, in flat state of the diaper 1, as for example shown in FIGS. 1, 2, 5 and 6 or may form an angle α of more than 0° to less than 90° or of 15° to 70°, or 30° to 60°, or 40° to 50° with a longitudinal line parallel to the longitudinal centerline Y of the diaper 1 in flat state of the diaper 1, as for example shown in FIGS. 3, 4 and 7. The cuff attachment areas 13 may be mirror images of one another in the longitudinal centerline Y of the diaper 1, in flat state of the diaper 1, as for example shown in FIGS. 1 to 7.

Typically, the cuff attachment areas 13 are no longer elastically extensible due to the attachment method. Hence, the elastic properties and behavior of the separator sheet 10 or separator sheet material 15 herein relate to the separator sheet 10 between the cuff attachment areas 13, or to the separator sheet material 15 prior to attachment.

Each cuff attachment area 13 may have an average transverse dimension of 3% to 40% or 5% to 35% or 5% to 25% of the average transverse dimension of the separator sheet 10. Each cuff attachment area 13 may have an average longitudinal dimension of 3 mm to 25 mm or 5 mm to 15 mm or 5 to 10 mm, Attachment of the Separator Sheet to the Topsheet Part(s) or all of the bottom edge portion 17 of the separator sheet 10 is/are attached to the topsheet 20, by adhesive bonding, pressure bonding, ultrasonic bonding or any other attachment mean known in the art. This may be in the front region A or crotch region B of the diaper 1 or topsheet 20. This may for example be done by one or more topsheet attachment area(s) 14, spaced apart with at least 5 mm, for example by one central topsheet attachment area 14 and two side topsheet attachment areas 14, on either transverse side of the topsheet central attachment area, as for example shown in FIGS. 1 to 7. The topsheet attachment area(s) 14 may comprise one or more individual bond(s). Such individual bond(s) may be arranged according to a certain bonding pattern. The bonding pattern density of at least one of (or each of) the topsheet attachment area(s) 14 may be more than 20%, or more than 30%, or more than 40%, or more than 60%, up to 100%.

It should be understood that if a topsheet attachment area 14 comprises more than one individual bond with a shortest distance of less than 3 mm between them, these are herein considered as a single unitary topsheet attachment area. The topsheet attachment areas 14 may have any shape. They may have a rectangular shape as for example shown in FIGS. 1 to 7. Such rectangular shaped topsheet attachment areas 14 may be oriented parallel to the longitudinal centerline Y of the diaper 1, in flat state of the diaper 1.

The separator sheet 10 has a first side 101 and a second side 102. The first side 101 may be attached to both the elastic cuffs 30*a*, 30*b* and the topsheet 20. Alternatively, the first side 101 may be attached to the elastic cuffs 30 and the second side 102 to the topsheet 20, as for example shown in FIGS. 1 to 5.

The topsheet attachment area(s) may be positioned closer to the front edge 1F of the diaper 1, or topsheet 20 or backsheet 21 than the cuff attachment areas 13*a*, 13*b*, as for example shown in FIGS. 1 to 5. This may reduce the risk that the separator sheet 10 creates a ramp which facilitatess the migration of the feces to the front of the diaper 1, Cuffs and Cuff Webs The diaper 1 has a pair of first and second longitudinally extending opposing elastic cuffs 30*a*, 30*b*, to which the separator sheet 10 (material 15) is attached.

It should be understood that a cuff 30*a*, 30*b* may be an individual cuff or a part of a cuff web, whereby such web is then subsequently divided into multitude of individual cuffs (e.g. travelling in MD in the process and extending in longitudinal direction in the diaper 1; thus the pair of cuffs 30*a*, 30*b* may be a pair of cuff webs. For the purpose of the invention, when referred to cuff or cuffs, this shall include cuff web or cuff webs, respectively, unless state otherwise.

Each of the cuffs 30*a*, 30*b* to which the separator sheet 10 is attached may be part of a unitary dual cuff sheet, comprising an outer cuff (leg cuff) and an inner cuff (barrier cuff), the latter being attached to the separator sheet 10.

Each cuff 30*a*, 30*b* has a longitudinally extending proximal edge that is joined to or attached to a diaper element, e.g. to the backsheet 21 or topsheet 20, or leg cuff, if present and an opposing, longitudinally extending, distal edge that is in use in contact with the skin of the wearer.

The cuffs 30*a*, 30*b* may be attached to the backsheet 21 adjacent and along the longitudinal sides of the backsheet 21 to have a cuff 30*a*, 30*b* on either side of the backsheet 21. The cuffs 30*a*, 30*b* may be attached to the topsheet 20, adjacent and along the longitudinal sides of the topsheet 20 to have a cuff 30*a*, 30*b* on either side of the topsheet 20.

The cuffs 30*a*, 30*b* may be mirror images of one another in the longitudinal centerline Y of the diaper 1, in flat state of the diaper. Each cuff 30*a*, 30*b* and/or its proximal edge may be curved or may be substantially straight.

The cuffs 30*a*, 30*b* may be made from a pair of cuff webs, comprising each a multitude of cuffs which are then separated from one another to form individual cuffs.

The cuffs 30*a*, 30*b* are elastic or elasticated, for example as described above with respect to the separator sheet 10 or separator sheet material 15. The cuffs 30*a*, 30*b* may be at least, or only, elasticated along the distal edge thereof. Each cuff 30*a*, 30*b* may be a sheet material with one or more elastic strands attached thereto in stretched state. The one or more elastic strands may extend at least along the distal edge of the cuff 301*a*, 301*b*.

The proximal edge of each cuff 30*a*, 30*b* may be positioned along a longitudinal side of the absorbent core 22 or of the backsheet 21 or of the topsheet 20.

The proximal edge of each cuff 30*a*, 30*b* may be positioned longitudinally outwards of the absorbent core 22, so that the whole absorbent core 22 is in between the cuff's proximal edges.

The cuffs 30*a*, 30*b* may be attached such that in use they have Z-direction orientation.

Figure 3:
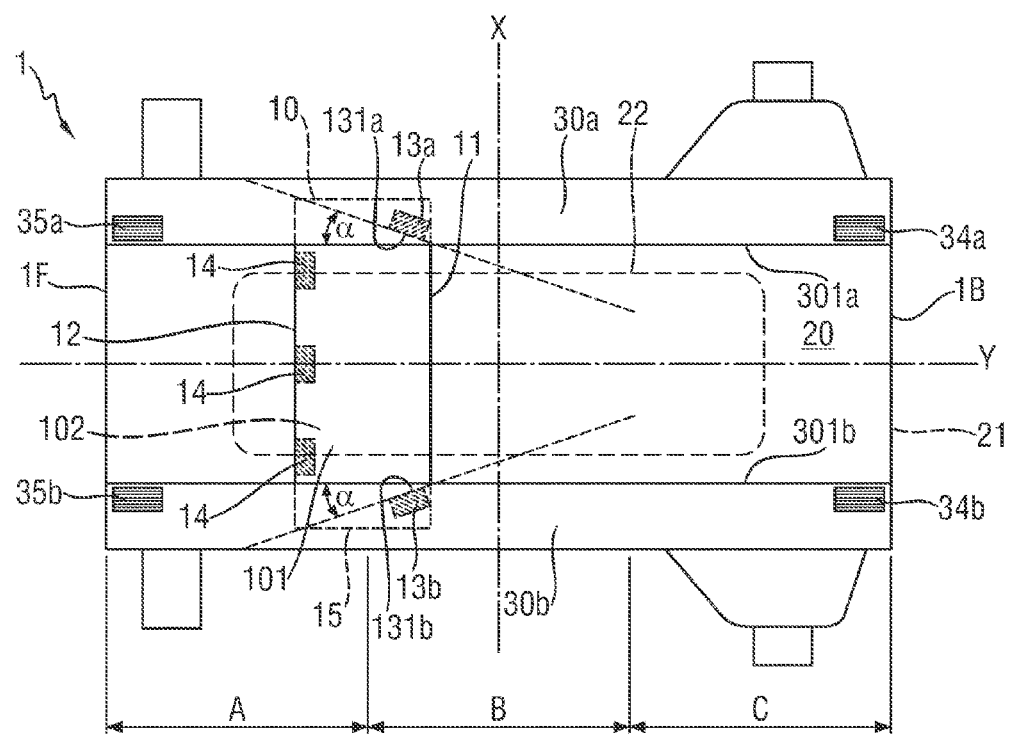
FIG. 3 shows a top view of a diaper according to another embodiment of the present invention in flat state.
Figure 4:
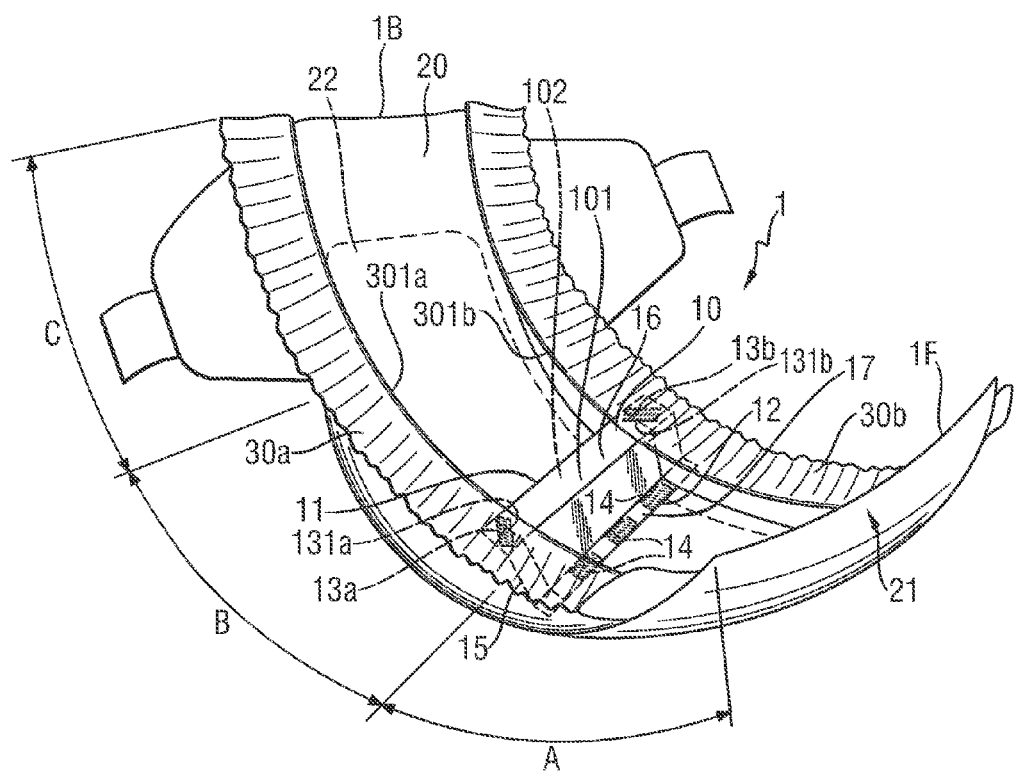
FIG. 4 shows a perspective view of the diaper of FIG. 3.
Figure 5:
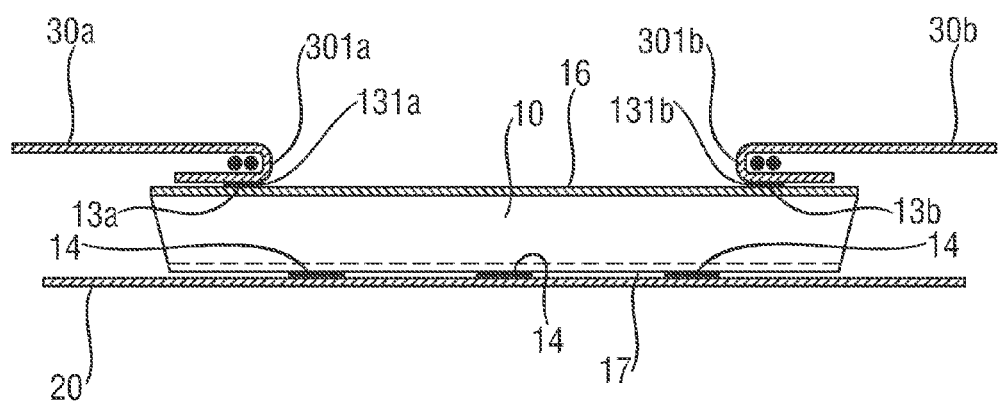
FIG. 5 shows a cross-sectional view of the diaper of FIG. 2 taken at the section line 2-2.
Figure 6:
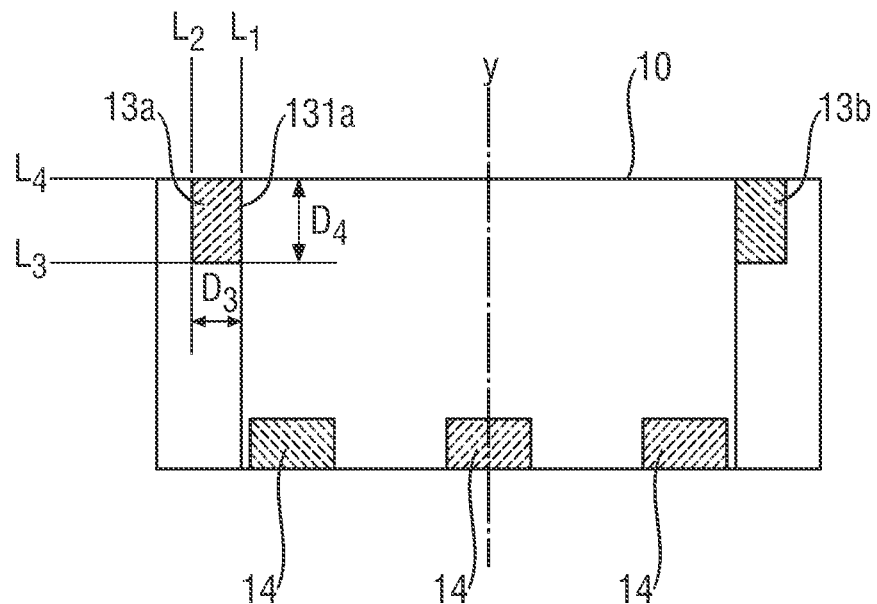
FIG. 6 shows a top view of the transverse separator sheet of FIG. 1 to illustrate how the projected bond length of a cuff attachment area is measured.
Figure 7:
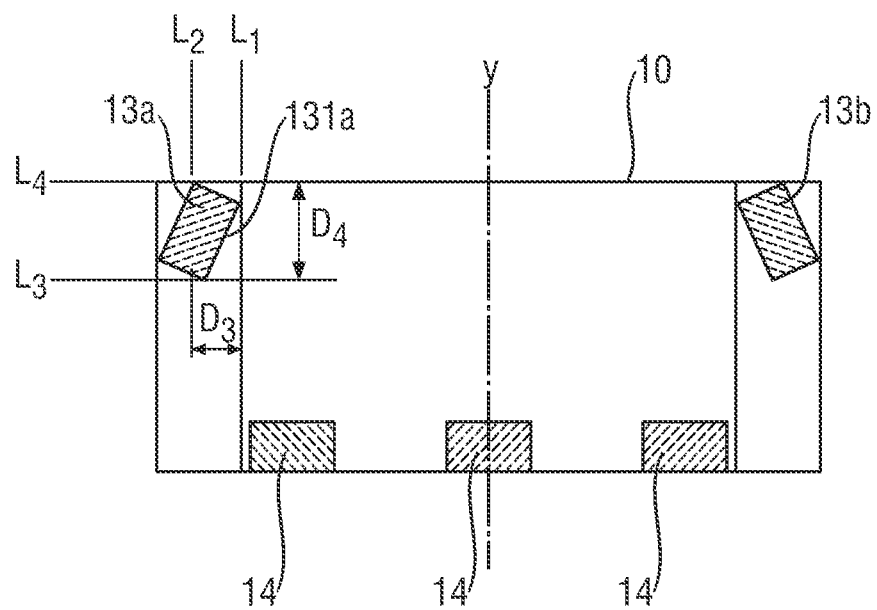
FIG. 7 shows a top view of the transverse separator sheet of FIG. 3 to illustrate how the projected bond length of a cuff attachment area is measured.

Each of the cuffs' distal edges 301*a*, 301*b* may be further attached in the back edge 1B (e.g. waistband) and/or front (e.g. waistband) edge 1F of the diaper 1, or the topsheet 20 or backsheet 21 respectively so-called front 35*a*, 35*b* and back 34*a*, 34*b* tack-down zones as for example shown in FIGS. 1 and 3.

The transverse distance between the front tackdown zone 35*a* of the first cuff 30*a* and the front tackdown zone 35*b* of the opposing second cuff 30*b* may equal the maximum transverse distance between the cuffs distal edges 301*a*, 301*b* in flat state of the diaper 1. This transverse distance may be the dimension $D_2$ described above, (e.g. when the cuffs 30*a*, 30*b* are attached substantially straight in the longitudinal direction). This transverse distance may be at least 5.0 cm, or at least 6.0 cm, or at least 7.0 cm. This transverse distance may be up to the average transverse dimension of the diaper 1 measured in the crotch region of the diaper 1, in flat state of the diaper 1. The same may apply to the transverse distance between the back tackdown zone 34*a* of the first cuff 30*a* and the back tackdown zone 34*b* of the opposing second cuff 30*b*.

Each cuff 30*a*, 30*b* may have an elastic tension of at least 20 grams (0.2N) and up to 100 grams (1.0N), or up to 50 grams (0.5N), when extended to a 95% or 80% extension strain.

The cuffs 30*a*, 30*b* or cuff web material may comprise a nonwoven sheet material. The same nonwoven sheet materials as the ones used to make the transverse separator sheet 10 may be used. The nonwoven sheet material may be a nonwoven barrier sheet material that is liquid impermeable, as known in the art, including for example nonwoven laminate(s) with one or more spunbond layers and/or carded layers, and one or more meltblown layers. The fibers used to form the nonwoven sheet material may be selected from polypropylene fibers, polyethylene fibers, bicomponent fibers, nano-fibers and any combinations thereof.

The cuffs 30a, 30b or part thereof and/or the separator sheet 10 or part thereof may comprise a skin care composition, e.g. lotion, as known in the art.

The separator sheet 10 or separator sheet material 15 may be attached to the cuffs 30a, 30b in relaxed, contracted state. The cuffs 30a, 30b may then be spread apart, thereby stretching the separator sheet 10 or separator sheet material 15.

The cuffs 30a, 30b may have any suitable dimensions, for example depending on the diaper-dimensions. They may extend about the hill length of the diaper 1. They may have a transverse dimension perpendicular to longitudinal centerline Y of the diaper 1 of for example at least 30 ram, or for example at least 40 mm.

Topsheet and Topsheet Web

The diaper 1 comprises a topsheet 20.

It should be understood that the topsheet 20 herein may be an individual topsheet or a topsheet that is part of a topsheet web, whereby such web is then subsequently divided into a multitude of individual topsheets. For the purpose of the invention, when referred to topsheet, this shall include a topsheet web, respectively, unless stated otherwise. The same applies for the backsheet 21 and absorbent core 22 (that may be a backsheet web or absorbent core web), as referred to herein.

The topsheet of the diaper 1 herein may be made of any suitable material known in the art, provided it allows urine to pass. Hereto, it may be made of a urine permeable material, including hydrophilic material, or material treated to be hydrophilic. It may be an apertured topsheet which comprise apertures to allow urine to pass to the absorbent core 22 under the topsheet 20;

The topsheet may be either hydrophilic or hydrophobic.

The separator sheet 10 or separator sheet material 15 may be attached to the cuffs 30a, 30b and to the topsheet 20 in relaxed, contracted state. The cuffs 30a, 30b may then be spread apart, thereby stretching the separator sheet 10 or separator sheet material 15; the cuffs 30a, 30b may for example be attached to the topsheet 20 prior to spreading or subsequent to the spreading step.

The topsheet 20 may be a stretchable material, or a material that is extensible, for example by the provision of folds. The topsheet 20 may for example comprise one or more longitudinally extending Z-fold(s) prior to attachments to the separator sheet 10 (or separator sheet material 15) and/or to the cuffs 30a, 30b. Once the topsheet 20 is unfolded, it no longer has the folds, e.g. Z-fold(s), but it may still have the longitudinally extending fold lines.

Preferred topsheet materials are nonwoven materials, including laminates and/or materials with apertures, such as apertured films, aperture formed films.

The topsheet 20, or for example only the crotch and/or back region thereof, may comprise a skin care composition, e.g. a lotion, as known in the art.

Other Elements of the Diaper

The diaper 1 has also at least a backsheet 21 and an absorbent core 22, the absorbent core 22 comprising for example multiple layers, including for example one or more acquisition layers, in liquid communication with the topsheet 20, and a storage layer, comprising superabsorbent polymer material/particles at least, typically enclosed by a core cover material.

The acquisition layer or layers may comprise any acquisition material which is capable of acquiring urine or runny feces, such as comminuted wood pulp, creped cellulose wadding; melt blown polymers, including coform; chemically stiffened, modified or cross-linked cellulosic fibers; tissue, including tissue wraps and tissue laminates; absorbent foams; absorbent sponges.

The storage layer may comprise any of the above material, but it typically at least comprises superabsorbent polymeric material/particles; for example, the absorbent storage layer may comprise more than 80% by weight (e.g. excluding core wrap) of superabsorbent polymeric (particulate) material; it may be free of cellulose (airfelt) material.

The backsheet 21 may be liquid impervious, as known in the art. The liquid impervious backsheet 21 preferably comprises a thin plastic film such as a thermoplastic film, for example having a thickness of about 0.01 mm to about 0.05 mm. Suitable backsheet materials comprise typically breathable material, which permit vapors to escape from the diaper 1 while still preventing exudates from passing through the backsheet 21. Suitable backsheet films include those manufactured by Tredegar Industries Inc. of Terre Haute, Ind. and sold under the trade names X15306, X10962 and X10964.

The backsheet 21, or any portion thereof, may be elastically extendable in one or more directions. The backsheet 21 may be attached or joined to a topsheet 20, the absorbent core 22, or any other element of the diaper 1 by any attachment means known in the art. It may be highly preferred that the longitudinal side edges of the topsheet 20 and backsheet 21 are directly attached to one another.

The diaper 1 may also include a sub-layer disposed between the topsheet 20 and the absorbent core 22, capable of accepting, and/or immobilizing bodily exudates, typically fecal material.

The diaper 1 herein may have a fastening system, typically joined to the waistband, as known in the art. Preferred fastening systems comprise fastening tabs and landing zones, wherein the fastening tabs are attached or joined to the back region of the diaper 1 and the landing zones are part of the front region A of the diaper 1.

The diaper 1 may be a pant-type diaper that has fastened side portions.

Process

The invention also relates to a process as described above, either for making a diaper 1 or a diaper portion, the diaper portion being a combination of a topsheet 20, cuffs 30a, 30b and separator sheet 10, that then may be combined with an absorbent core 22 and backsheet 21, and optionally further elements, such as side panels/ears, fasteners, leg cuffs, etc.

The process of the invention requires spreading of the cuffs 30a, 30b to which the separator sheet material 15 is attached in contracted, relaxed state and thereby stretching of the separator sheet 10. It may be easier from a process point of view to attach the separator sheet material 15 in contracted, relaxed state to the cuffs 30a, 30b. The cuffs 30a, 30b are spaced apart an average transverse distance $D_1$ in the crotch region before spreading, when the separator sheet 10 is attached, and an average transverse distance $D_2$ in the crotch region, after spreading. $D_2$ may be at least 1.8 times $D_1$, or at least 2.2 times $D_1$, or at least 2.4 times $D_1$, or at least 2.8 times $D_1$, or at least 3.0 times $D_1$, or at least 3.3 times $D_1$, or at least 4.0 times $D_1$. $D_2$ may be at least 5.0 cm, or at least 6.0 cm, or at least 7.0 cm. $D_2$ may be up to the average transverse dimension of the diaper 1 measured in the crotch region B of the diaper 1.

The cuffs 30a, 30b may then be attached to a further diaper element, such as the topsheet 20 or backsheet 21 or leg cuffs if present. Alternatively, the cuffs 30a, 30b may already be attached to a further diaper 1 element before spreading, e.g. to the topsheet 20, and then this further diaper element may also be expanded or stretched during spreading. As described hereinbefore, the topsheet 20 may be extensible or comprise one or more longitudinally extending Z-folds before spreading, to allow expansion of the fold(s) during spreading of the cuffs 30a, 30b.

The process also comprises the step of attaching the separator sheet material 15 to the topsheet 20. This may be done simultaneous with, subsequent to, or prior to the attachment to the cuffs 30a, 30b. It may be preferred to attach the separator sheet material 15 to the topsheet 20 in contracted, relaxed state.

The attachment of the separator sheet material 15 to the topsheet 20 may be done in two or more steps, and in two or more topsheet attachment areas 14, e.g. first in contracted state, prior or simultaneously or subsequent to the attachment of the separator sheet material 15 to the cuffs 30a, 30b, in a first topsheet attachment area 14, and then subsequently, e.g. in stretched state, attachment in one or more additional areas (e.g. on either side of the first topsheet attachment area 14).

All features with respect to the separator sheet 10 and sheet material 15, elastic cuffs, attachment areas and topsheet etc. described above are equally relevant for the process of the invention.

Test Methods
Two Cycle Hysteresis Tests (In-Use and In-Process):
Equipment and Preparation of Samples:

Suitable instruments for this test include tensile testers commercially available from MTS Systems Corp., Eden Prairie, Minn. (e.g. Alliance RT/1 or Sintech 1/S) or from Instron Engineering Corp., Canton, Mass. or from Zwick/Roell, Kennesaw, Georgia/Ulm, Germany.

The tester is equipped with a grip face set in the upper and lower grips, where each set has one rubber-coated face (80 A shore hardness) and one contact line face (metal), with a screw mechanism that engages the contact line face into the rubber-coated face to prevent slippage. The length of the upper and lower grips is at least as long as the clamped length of the specimen to be tested, the grip length being the dimension of the grip parallel to the length of the specimen. A load cell is used so that the maximum load measured is within 10-90% of the maximum capacity of the load cell. The instrument is calibrated according to the manufacturer's specification.

Before obtaining the specimen from the diaper, the diaper is kept in a relaxed state at ambient temperature (22° C.+/−5° C.) for at least 24 hours.

The separator sheet 10 is cut to obtain a rectangular specimen having a transverse dimension (width) of 20 mm centered on the longitudinal centerline Y of the diaper 1 and a longitudinal dimension (length) of 30 mm, both transverse and longitudinal dimensions being measured in relaxed, contracted state of the specimen when the specimen is laid out flat onto an even horizontal surface. The transverse dimension and longitudinal dimension of the specimen are measured parallel to respectively the transverse dimension and longitudinal dimension of the separator sheet 10. The transversely extending edge of the specimen which is the closest to the top edge 11 of the separator sheet 10 is referred hereinafter as the top edge of the specimen. The opposite transversely extending edge of the specimen is referred hereinafter as the bottom edge of the specimen.

For separator sheet(s) 10 that has/have a minimum longitudinal dimension in relaxed, contracted state of the separator sheet(s) 10 between the top edge and the bottom edge of the separator sheet(s) of more than 30 mm, the specimen is cut such that it does include the top edge of the separator sheet 10.

Clamped Length

The clamped length is the longitudinal dimension of the specimen in relaxed, contracted state which is clamped between the grips starting from the top edge of the specimen. The clamped length is equal to the projected bond length of the cuff attachment areas 13. The projected bond length of the cuff attachment areas 13 is measured (as described hereinafter) prior to cutting of the test specimen.

The diaper 1 is laid out flat onto an even horizontal surface. A first longitudinally extending line $L_1$ parallel to the longitudinal centerline Y of the diaper 1 and in contact with the point of the cuff attachment area 13 which is the closest to the longitudinal centerline Y of the diaper 1 is drawn, as for example shown in FIGS. 6 and 7. A second longitudinally extending line $L_2$ parallel to the first longitudinally extending line $L_1$ is drawn further away from the longitudinal centerline Y with a distance $D_3$ between the first and the second longitudinally extending lines $L_1$, $L_2$ of 5 mm, as for example shown in FIGS. 6 and 7. A first laterally extending line $L_3$ perpendicular to the longitudinal centerline Y of the diaper 1 and in contact with the point of the cuff attachment area 13 which is the closest to the front edge 1F of the diaper 1 and laterally comprised between the first and the second longitudinally extending lines $L_1$, $L_2$ is drawn, as for example shown in FIGS. 6 and 7. A second laterally extending line $L_4$ perpendicular to the longitudinal centerline Y of the diaper 1 and in contact with the point of the cuff attachment area 13 which is the closest to the back edge 1B of the diaper 1 and laterally comprised between the first and the second longitudinally extending lines $L_1$, $L_2$ is drawn as for example shown in FIGS. 6 and 7.

The distance $D_4$ between the first and second laterally extending lines $L_3$, $L_4$ corresponds to the projected bond length of the cuff attachment area 13.

For embodiments wherein the cuff attachment areas 13 are not mirror images of one another in the longitudinal centerline Y of the diaper 1 when the diaper 1 is laid out flat, the projected bond length of the cuff attachment areas 13 corresponds to the average of the projected bond lengths of the first and second cuff attachment areas 13.

Before starting the test (details below), each specimen and the equipment must equilibrate at 22° C. (+/−1° C.), for at least 1 hour, for the in-process and the in-use two cycle hysteresis tests herein. For the in-use two-cycle hysteresis test (to be done at 34° C.), each specimen and the equipment must also equilibrate for at least 5 minutes and up to 10 minutes at 34° C. (+/−1° C.) immediately prior to initiating the test.

The force reading on the instrument is zeroed to account for the mass of the fixtures and grips. The specimen is mounted into the grips with no slack and the force measured is between 0.00 N and 0.01 N. The data acquisition frequency is 50 Hz for the in-use two-cycle hysteresis test and 100 Hz for the in-process two-cycle hysteresis test; the force, time and engineering strain data are acquired during all segments of the hysteresis tests.

The specimen is mounted with 10 mm of its width in relaxed, contracted state between the lines of contact of the grips (gauge width) and 5 mm of its width outside the line of contact of each grip. The clamped length of the specimen is clamped in the grips. The remaining length of the specimen (which equals the length of the specimen minus the clamped length) is excluded from the grips. The clamped length is specified above.

In the following, engineering strain is defined as $\Delta W/W_0$ with $\Delta W=W_t-W_0$, wherein $W_0$ is the initial sample width and $W_t$ is the sample width at time t.

In-Use Two-Cycle Hysteresis Test (Measurement at 34° C.):
The In-Use Two-cycle Hysteresis Test is Performed as Follows:
1. Slack Adjustment: Move the crosshead at a speed of 13 min/minute until the slack adjustment preload force of 0.02 N is achieved. The distance between the lines of contact of the grips at the slack adjustment preload force of 0.02N is the adjusted gauge width $W_{GAdj}$ which is equal to the initial sample width $W_0$ (engineering strain=0%).
2. First Cycle:
The specimen is extended to the tested engineering strain at a crosshead speed of 100 min/min, and held at this engineering strain for 60 seconds. The crosshead is then returned to the adjusted gauge width $W_{GAdj}$ at a crosshead speed of 100 mm/min, and held at this adjusted gauge width $W_{GAdj}$ for 60 seconds.
3. Second Cycle:
The specimen is extended to the same engineering strain as the engineering strain in the first cycle, at a crosshead speed of 100 mm/min, and held at this engineering strain for 60 seconds. The crosshead is then returned to the adjusted gauge width $W_{GAdj}$ at a crosshead speed of 100 min/min, and held at this adjusted gauge width $W_{GAdj}$ for 60 seconds.

The force, time and engineering strain data are acquired for all segments of the in-use two cycle hysteresis test at a frequency of 50 Hz. The percent set (% Set) is defined as the engineering strain, in percent, where the $2^{nd}$ cycle extension force of 0.069 N (7 gram-force) is measured.

A minimum of 5 specimens are measured, to determine the average test values, average data being provided by the tensile tester test software (e.g. Alliance RT1 MTS Instrument is TestWorks4 version 4.08B)

The method report specifies the tested engineering strain, the specimen dimensions and the clamped length used for the measurements.

The properties of the separator sheet reported for the method are the $1^{st}$ cycle extension force at the tested engineering strain and the % set.

In-Process Two-Cycle Hysteresis Test (Measurement at 22° C.):
The In-Process Two-cycle Hysteresis Test is Performed as Follows:
1. Slack Adjustment: Same as step 1 above for the In-Use Two-Cycle Hysteresis Test.
2. First Cycle:
The specimen is extended to the tested engineering strain at a crosshead speed of 800 mm/min. There is no hold at this engineering strain. The crosshead is then returned to the adjusted gauge width $W_{GAdj}$ at a crosshead speed of 800 min/min, and held at this engineering strain for 60 seconds.
3. Second Cycle:
The specimen is extended to the same engineering strain as the engineering strain in the first cycle, at a crosshead speed of 800 mm/min. There is no hold at this engineering strain. The crosshead is then returned to the adjusted gauge width $W_{GAdj}$ at a crosshead speed of 800 min/min and held at this engineering strain for 60 seconds.

Each specimen of separator sheet of the diaper is inspected for damage after the In-Process two-cycle hysteresis test. Separator sheet material of the invention must have no damage after the test. The damage is defined via the percent set. The percent set (% Set) is defined as the engineering strain, in percent, where the $2^{nd}$ cycle extension force of 0.069 N (7 gram-force) is measured. If the percent set is lower than 30%, the specimen is considered as not being damaged and is therefore considered as being elastically extensible to tested engineering strain.

A minimum of 5 specimens are measured, to determine the average test values, average data being provided by the tensile tester test software (e.g. Alliance RT1 MTS Instrument is TestWorks4 version 4.08B)

The method report specifies the used engineering strain, the specimen dimensions and the clamped length used for the measurements.

The property of the separator sheet reported for the method is the % set.

EXAMPLES

Four different diapers comprising a transverse separator sheet are prepared. Each of the four diapers is a Pampers Active Fit™ size 4 diaper commercially available in Germany in June 2012 to which a transverse separator sheet is attached. Each of the four diapers comprises a first and a second cuff attachment area wherein the top edge portion of the separator sheet is attached by pressure bonding to the crotch region of the elastic cuffs of the diaper and one topsheet attachment area wherein the bottom edge portion of the separator sheet is attached by pressure bonding to the topsheet of the diaper.

The first and second cuff attachment areas have a rectangular shape with a longitudinal dimension of 15 mm and a lateral dimension of 13 mm and are oriented parallel to the longitudinal centerline Y of the diaper and are mirror images of one another in the longitudinal centerline Y of the diaper, in flat state of the diaper. The topsheet attachment area has a rectangular shape with a longitudinal dimension of 6 mm and a lateral dimension of 75 mm and is oriented parallel to the lateral centerline X of the diaper.

Each of the four diapers is made of a different separator sheet material as described hereinafter. Each of the separator sheet material is rectangular and has a longitudinal dimension of 85 mm and a transverse dimension of 100 mm when laid out flat onto an even horizontal surface in relaxed, contracted state and is oriented such that the separator sheet material is extensible in the transverse direction.

Examples 1 to 3

The transverse separator sheets of the diapers of examples 1, 2 and 3 are made of the activated trilaminate separator sheet materials shown in Table 1.

The activated trilaminate separator sheet materials, shown in Table 1, are made by adhesive lamination of an extrusion bilaminate (EBL, NW1/A1/B1/A2) to a second nonwoven (NW2), followed by activation to release the stretch.

EBL useful in the present invention are disclosed in U.S. Pat. No. 8,168,853, by Autran, etc., and are made by Clopay Plastic Product of Mason, Ohio. The EBL is made by bringing one nonwoven (NW1) onto a freshly extruded and drawn-down multilayer (A1/B1/A2) in close contact to each other at the nip of two compression rolls wider controlled temperature and pressure conditions to form a bond between the tie layer (A1) of the extruded multilayer film (A1/B1/A2) and the fibers of the nonwoven (NW1).

The EBL comprises a first nonwoven (NW1) and a 15 gsm multilayer film comprising a tie layer (A1), an inner layer (B1), and a skin layer (A2). The composition of the film inner layer (B1) for examples 1 and 2 is a weight % blend of 92% Vistamaxx 6102, 1% Ampacet 10562 (process aid) and 7% Ampacet 110361 (white masterbatch with 70%

TiO$_2$). The composition of the film inner layer (B1) of the EBL of example 3 is a weight % blend of 87% Vistamaxx 6102, 5% Inspire Dow 118 PP, 1% Ampacet 10562 and 7% Ampacet 110361. The composition of A1 is compositionally identical to A2 and is a weight % blend of 24% Infuse 9107, 75% Elite 5800, and 1% Ampacet 10562.

The first nonwoven (NW1) used in the EBL of examples 1, 2 and 3 is a 15 gsm spunbond bicomponent PP/PE (50/50, core/sheath) nonwoven from Pegas Nonwovens (Czech Republic). The second nonwoven (NW2) adhesively laminated to the EBL of examples 1 and 2 is a 20 gsm spunbond bicomponent PP/PE (70/30, core/sheath) nonwoven from Fiberweb (Washougal, Wash.), while in example 3, the second nonwoven (NW2) is made of the same nonwoven as the first nomAioven (NW1), a 15 gsm spunbond bicomponent PP/PE (50/50, core/sheath) nonwoven from Pegas Nonwovens (Czech Republic). Vistamaxx 6102 resin is available from ExxonMobil Chemical Company of Houston, Tex. Ampacet 10562 and 110361 are available from Ampacet Corporation of Cincinnati, Ohio. Elite 5800 PE and Infuse 9107 resins are available from The Dow Chemical Company of Midland, Mich.

For examples 1, 2 and 3, the aged roll of EBL is combined with the second nonwoven (NW2) using a high speed adhesive lamination process, with the addition of approximately 4.5 gsm of Bostik H2861 adhesive (commercially available from Bostik Inc. of Wauwatosa, Wis.) to the A2-NW2 interface to form a trilaminate. For examples 1 and 3, the lamination is followed by mechanical activation by a ring, rolling activation process. For example 2, the lamination is followed by mechanical activation by High Speed Research Press (HSRP) activation. Lamination and activation details are shown in Table 1.

HSRP activation process is described in U.S. Pat. Nos. 7,062,983 and 6,843,134. HSRP activation process refers to the use of aluminum plates with inter-meshing teeth to selectively stretch portions of the trilaminate such that the nonwoven layers are broken and/or elongated and the elastic multilayer film is able to extend and retract without being unduly encumbered by the nonwoven layers. The activation plates used for the HSRP activation have inter-meshing teeth with a tip radius of 0.1 mm, a root radius of 0.5 mm and tooth height of 10.15 mm.

TABLE 1

Examples of activated trilaminate separator sheet materials

| | Examples | | |
|---|---|---|---|
| | 1 | 2 | 3 |
| Trilaminate Structure = adhesive free bilaminate NW1/A1/B1/A2 + 4.5 gsm H2861 adhesive + NW2 | | | |
| NW1 | 1[1] | 1 | 1 |
| A1 = A2 | Infuse/PE blend[3] | Infuse/PE blend | Infuse/PE blend |
| B1 | VM blend-1[4] | VM blend-1[4] | VM blend-2[5] |
| NW2 | 2[2] | 2 | 1 |
| total film basis weight | 15 gsm | 15 gsm | 15 gsm |
| multilayer film structure | A1/B1/A2 | A1/B1/A2 | A1/B1/A2 |
| Details of adhesive lamination (combining bilaminate + NW) and activation | | | |
| Interface with Adhesive | A2-NW2 | A2-NW2 | A2-NW2 |
| Adhesive type (Bostik) | H2861 | H2861 | H2861 |
| Adhesive basis weight (gsm) | 4.5 gsm | 4.5 gsm | 4.5 gsm |
| Nip Gap | 0.005" | 0.005" | 0.005" |
| lamination line speed (m/sec) | 5.4 | 5.4 | 6.1 |
| activation type | on line @ 5.4 m/sec | HSRP @ 0.3 m/sec with 250 millisecond dwell time | on line @ 6.1 m/sec |
| activation pitch, inches (mm) | 0.100" (2.54 mm) | 0.098" (2.49 mm) | 0.100" (2.54 mm) |
| Depth of engagement, DOE, inches (mm) | 0.160" (4.06 mm) | 0.220" (5.59 mm) | 0.200" (5.08 mm) |
| Average Strain of activation (%) | 240% | 364% | 318% |

[1] NW = 1 = 15 gsm (50/50 core/sheath, PP/PE) bicomponent spunbond, produced at Pegas Nonwovens (Czech Republic).
[2] NW = 2 = 20 gsm (70/30 core/sheath, PP/PE) bicomponent spunbond, produced at Fiberweb (Washougal, Washington).
[3] Infuse/PE blend = Infuse 9107 (24%), Elite 5800 PE (75%), Ampacet 10562 (1%) in weight %.
[4] VM blend-1 = Vistamaxx 6102 (92%), Ampacet 10562 (1%), Ampacet 110361 (7%) in weight %.
[5] VM blend-2 = Vistamaxx 6102 (87%), Dow 118 PP (5%), Ampacet 10562 (1%), Ampacet 110361 (7%) in weight %.

Example 4

The transverse separator sheet of the diapers of example 4 is made of the back ear material of Pampers Active Fit™ diapers commercially available in Germany in June 2012.

Ten samples of each of the diapers of examples 1 to 4 are prepared. The separator sheet of each of the ten samples is cut to obtain a rectangular specimen having a width of 20 mm centered on the longitudinal centerline (Y) of the diaper (1) and a length of 30 mm, both measured in relaxed, contracted state of the specimen, when the specimen is laid out flat onto an even horizontal surface. The clamped length of all samples is 15 mm. Five of the samples are tested according to the in-use two-cycle hysteresis test and five of the samples are tested according to the in-process two-cycle hysteresis test. For the in-use two-cycle hysteresis test, the engineering strain to which the specimens are extended is of 1.2 whereas for the in-process two-cycle hysteresis test, the engineering strain is 2.0. The average values for the first cycle extension forces at which an engineering strain of 0.8 and of 1.2 is reached and the percent sets measured according to the in-use two-cycle hysteresis test are summarized in Table 2 below. The average values for the percent sets measured according to the in-process two-cycle hysteresis test are summarized in Table 3 below.

TABLE 2

| | Examples | | | |
|---|---|---|---|---|
| | 1 | 2 | 3 | 4 |
| First cycle extension force at which an engineering strain of 0.8 is reached (N) | 0.7 | 0.5 | 0.7 | 1.7 |
| First cycle extension force at which an engineering strain of 1.2 is reached (N) | 1.1 | 0.7 | 0.9 | 2.2 |
| Percent set at 0.069 N | 15 | 13 | 18 | 9 |

As can be seen in Table 2, the transverse separator sheets of the diapers of examples 1, 2 and 3 have an engineering strain of 0.8 at a first cycle extension force of less than 1.0N. Such a low first cycle extension force ensure that the elastic cuffs, to which the separator sheets are attached in use, are not pulled too close together, leading to potential leakage issues of urine or feces outside or onto the cuffs. Furthermore, die cuffs can expand and move outwards without being too restricted by die elastic forces of the separator sheets, when the wearer spreads the legs. The low percent set values ensure that the transverse separator sheets of the diapers of examples 1, 2 and 3 are such that in use, when the wearer moves the legs together, the transverse separator sheets can contract to a very small dimension very quickly, thus avoiding stack in the separator sheets, and hence reducing the risk of feces leakage over the separator sheets.

TABLE 3

| | Examples | | | |
|---|---|---|---|---|
| | 1 | 2 | 3 | 4 |
| Elastic extensibility to an engineering strain of at least 0.8 | Yes | Yes | Yes | Yes |
| Elastic extensibility to an engineering strain of at least 1.2 | Yes | Yes | Yes | Yes |
| Elastic extensibility to an engineering strain of at least 2.0 | Yes | Yes | Yes | Yes |
| Percent set at 0.069 N | 20 | 18 | 24 | 15 |

As can be seen in Table 3, the percent set measured according to the in-process two-cycle hysteresis test is lower than 30% which demonstrates that the transverse separator sheets of the diapers of examples 1, 2, 3 and 4 are elastically extensible in the transverse direction to an engineering strain of at least 2.0 and are therefore also elastically extensible to an engineering strain of at least 1.2 and at least 0.8. Such separator sheets can consequently be processed in a process that requires high extension and are also able to contract about immediately to about their original width after having been stretched.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An infant or adult diaper having a longitudinal centerline and a lateral centerline perpendicular to the longitudinal centerline, a diaper front edge and a diaper rear edge, wherein the diaper comprises a topsheet and a backsheet and positioned therein between an absorbent core having front and rear core edges, and a first and second longitudinally extending opposing elastic cuffs, positioned on either longitudinal side of the topsheet, each of the diaper, topsheet, backsheet, absorbent core and elastic cuffs having a crotch region, positioned in between a front region and a back region, wherein the diaper comprises a transverse separator sheet made of a separator sheet material, the transverse separator sheet having a transversely extending top edge and top edge portion and an opposing transversely extending bottom edge and bottom edge portion, wherein parts of the top edge portion are attached to the cuffs in the respective crotch regions or front regions of the cuffs at a first cuff attachment area and a second opposing cuff attachment area, each cuff attachment area having an inner edge towards the longitudinal centerline of the diaper; and at least part of the bottom edge portion is attached to the topsheet at at least one topsheet attachment area, the topsheet attachment area being forward of and spaced from the rear edge of the absorbent core, and being positioned closer to the diaper front edge than are the cuff attachment areas, whereby the separator sheets minimum transverse dimension in relaxed state of the separator sheet between the opposing inner edges of the first and second cuff attachment areas is at least 20 mm and whereby the separator sheets minimum longitudinal dimension in relaxed state of the separator sheet between the top edge and the bottom edge of the separator sheet is at least 30 mm; and the transverse separator sheet:

has a transverse strain of 0.8 at a first cycle extension force of 1.0N or less, as measured according to the in-use two-cycle hysteresis test described herein; and has 30% set or less after having been extended to a transverse strain of 0.8, as measured according to the in-use two-cycle hysteresis test; and is elastically extensible in the transverse direction to a strain of at least 0.8, as measured according to the in-process two-cycle hysteresis test described herein at 22° C.

2. The diaper according to claim 1, whereby the transverse separator sheet has a transverse strain of 0.8 at a first cycle extension force of 0.8N or less, as measured according to the in-use two-cycle hysteresis test.

3. The diaper according to claim 1, whereby the transverse separator sheet is elastically extensible in the transverse direction to a strain of at least 1.2, as measured according to the in-process two-cycle hysteresis test at 22° C.

4. The diaper according to claim 1, whereby the transverse separator sheet is elastically extensible in the transverse direction to a strain of at least 2.0, as measured according to the in-process two-cycle hysteresis test at 22° C.

5. The diaper according to claim 1, whereby the transverse separator sheet:
  has a transverse strain of 1.2 at a first cycle extension force of 1.5N or less, or 1.0N or less, or 0.8N or less, as measured according to the in-use two-cycle hysteresis test; and
  has 30% set or less after having been extended to a transverse strain of 1.2, as measured according to the in-use two-cycle hysteresis test.

6. The diaper according to claim 1, whereby the separator sheets minimum transverse dimension in relaxed state of the separator sheet between the opposing inner edges of the first and second cuff attachment areas is up to 55 mm.

7. The diaper according to claim 1, whereby the separator sheets minimum longitudinal dimension in relaxed state of the separator sheet between the top edge and the bottom edge of the separator sheet is at least 40 mm.

8. The diaper according to claim 1, whereby the separator sheet material is or comprises an elastic film or a nonwoven sheet material or a laminate of an elastic film and a nonwoven sheet material or comprises one or more elastic band(s) or strand(s).

\* \* \* \* \*